(12) United States Patent
Debrie et al.

(10) Patent No.: US 12,403,188 B2
(45) Date of Patent: Sep. 2, 2025

(54) *BORDETELLA* STRAINS EXPRESSING SEROTYPE 3 FIMBRIAE

(71) Applicants: Institut Pasteur de Lille, Lille (FR); Institut National de la Santé et de la Recherche Médicale (INSERM), Paris (FR)

(72) Inventors: Anne-Sophie Debrie, La Madeleine (FR); Dominique Raze, Gruson (FR); Camille Locht, Brussels (BE)

( * ) Notice: Subject to any disclaimer, the term of this patent is extended or adjusted under 35 U.S.C. 154(b) by 513 days.

(21) Appl. No.: 17/817,272

(22) Filed: Aug. 3, 2022

(65) Prior Publication Data

US 2022/0362369 A1 Nov. 17, 2022

Related U.S. Application Data

(60) Division of application No. 16/848,793, filed on Apr. 14, 2020, now Pat. No. 11,446,372, which is a continuation of application No. PCT/EP2018/078522, filed on Oct. 18, 2018.

(60) Provisional application No. 62/574,068, filed on Oct. 18, 2017.

(51) Int. Cl.
*A61K 39/10* (2006.01)
*A61K 39/02* (2006.01)
*A61P 31/04* (2006.01)
*C12P 21/06* (2006.01)
*A61K 39/00* (2006.01)

(52) U.S. Cl.
CPC ............ *A61K 39/099* (2013.01); *A61P 31/04* (2018.01); *A61K 2039/522* (2013.01)

(58) Field of Classification Search
None
See application file for complete search history.

(56) References Cited

U.S. PATENT DOCUMENTS 5,395,764 A 3/1995 Riboli et al.

FOREIGN PATENT DOCUMENTS

EP 1184459 3/2002

OTHER PUBLICATIONS

Locht, Camille: "Molecular aspects of *Bordetella pertussis* pathogenesis," Internatl Microbiol, 1999, vol. 2:137-144.
Williams, Margaret M. et al: "*Bordetella pertussis* Strain Lacking Pertactin and Pertussis Toxin," Emerging Infectious Diseases, Feb. 2016, vol. 22, No. 2: 319-322.
Moriuchi, Takumi et al: "Research on *Bordetella pertussis* and *Bordetella holmesii*," National Institute of Infectious Diseases Report, 2017, pp. 1-18; (English translation of the relevant sections only).
Heikkinen, Eriikka et al: "*Bordetella pertussis* isolates in Finland: Serotype and fimbrial expression," BMC Microbiology, 2008, vol. 8, No. 162:1-9.
Schnoeller, Corinna et al.: "Attenuated *Bordetella pertussis* Vaccine Protects against Respiratory Syncytial Virus Disease via an IL-17-Dependent Mechanism," American Journal of Respiratory and Critical Care Medicine, Jan. 15, 2014, vol. 189, No. 2:194-202.

*Primary Examiner* — Jennifer E Graser
(74) *Attorney, Agent, or Firm* — Stanley A. Kim

(57) ABSTRACT

A Fim3-producing BPZE1 derivative with sufficiently stable fim3 expression to provide improved protection in mice against Fim3-only producing clinical *B. pertussis* isolates was developed. The fim3 expression in BPZE1f3 did not alter the protective efficacy against Fim2+ strains, nor against strains that produce neither Fim2 nor Fim3.

6 Claims, 6 Drawing Sheets

Specification includes a Sequence Listing.

SEQUENCE LISTING

```
Sequence total quantity: 6
SEQ ID NO: 1            moltype = DNA  length = 36
FEATURE                 Location/Qualifiers
source                  1..36
                        mol_type = other DNA
                        organism = synthetic construct
                        note = Description of Artificial Sequence: Synthetic
                        oligonucleotide
SEQUENCE: 1
gagctcttta ccgcggccgc cagttgttca tcaatg                                   36

SEQ ID NO: 2            moltype = DNA  length = 24
FEATURE                 Location/Qualifiers
source                  1..24
                        mol_type = other DNA
                        organism = synthetic construct
                        note = Description of Artificial Sequence: Synthetic
                        oligonucleotide
SEQUENCE: 2
ggatccatca tcgagaccga ctgg                                                24

SEQ ID NO: 3            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 3
agctaggggt agaccacgga                                                     20

SEQ ID NO: 4            moltype = DNA  length = 20
FEATURE                 Location/Qualifiers
source                  1..20
                        mol_type = other DNA
                        organism = synthetic construct
                        note = Description of Artificial Sequence: Synthetic primer
```

```
SEQUENCE: 4
ataactcttc tggcgccaag                                                      20

SEQ ID NO: 5          moltype = DNA  length = 20
FEATURE               Location/Qualifiers
source                1..20
                      mol_type = other DNA
                      organism = synthetic construct
                      note = Description of Artificial Sequence: Synthetic primer
SEQUENCE: 5
catgacggca cccctcagta                                                      20

SEQ ID NO: 6          moltype = DNA  length = 20
FEATURE               Location/Qualifiers
source                1..20
                      mol_type = other DNA
                      organism = synthetic construct
                      note = Description of Artificial Sequence: Synthetic primer
SEQUENCE: 6
ttcacgtacg aggcgagata                                                      20
```

BORDETELLA STRAINS EXPRESSING SEROTYPE 3 FIMBRIAE

CROSS-REFERENCE TO RELATED APPLICATIONS

The present application is a divisional of U.S. nonprovisional patent application Ser. No. 16/848,793 which was filed on Apr. 14, 2020 as a by-pass continuation under 35 U.S.C. 111(a) of international patent application number PCT/EP2018/078522 filed on Oct. 18, 2018 which claims the priority of U.S. provisional patent application serial number 62/574,068 filed on Oct. 18, 2017.

SEQUENCE LISTING

The instant application contains a Sequence Listing which has been submitted electronically in XML file format and is hereby incorporated by reference in its entirety. Said XML copy, created on Aug. 3, 2022, is named 7056-0143_SL.xml and is 7,427 bytes in size.

STATEMENT AS TO FEDERALLY SPONSORED RESEARCH

Not applicable.

FIELD OF THE INVENTION

The invention relates generally to the fields of microbiology, immunology, vaccinology, sero-epidemiology, biochemistry and medicine. More particularly, the invention relates to live attenuated *Bordetella* strains modified to express serotype 3 fimbriae and their use in vaccines.

BACKGROUND

Whooping cough or pertussis is a severe respiratory disease that can be life-threatening, especially in young infants, and its incidence is on the rise in several countries, despite a global vaccination coverage of >85%, according to the World Health Organization. However, it also affects adolescents and adults, where symptoms are usually atypical, and therefore the disease often remains undiagnosed in these age groups. Nevertheless, adolescents and adults, even if they remain asymptomatic, can transmit the causative agent *Bordetella pertussis* to young infants before they are protected by the primary vaccination series. In fact, a recent wavelet analysis of *B. pertussis* infection in the US and the UK, combined with a phylodynamic analysis of clinical isolates showed that asymptomatic transmission is the principle cause of the recent pertussis resurgence. In addition, asymptomatic *B. pertussis* infection may not be anodyne, as epidemiological evidence suggests that *B. pertussis* infection may be related to auto-immune diseases, such as Celiac disease, multiple sclerosis, and even Alzheimer's disease Currently available whole-cell or acellular vaccines have been very effective in reducing the incidence of whooping cough after three primary vaccination doses. However, in contrast to prior infection with *B. pertussis*, they are much less effective in reducing asymptomatic colonization, as shown in the recently established baboon model. Although vaccinated baboons were protected against pertussis disease upon experimental infection with *B. pertussis*, they could readily be infected and transmit the organism to littermates, even in the absence of symptoms, in contrast to convalescent baboons. Altogether these observations illustrate the shortcomings of currently available vaccines, and call for new vaccines that protect both against disease and infection.

Based on the observation that the best way to protect against *B. pertussis* colonization is prior infection, a live attenuated vaccine has been developed that can be administered by the nasal route, in order to mimic as much as possible natural infection without causing disease. The vaccine strain, called BPZE1, lacks the gene coding for dermonecrotic toxin, produces genetically detoxified pertussis toxin and is deficient for tracheal cytotoxin production by the replacement of the *B. pertussis* ampG gene with the *Escherichia coli* ampG gene. BPZE1 has been shown to be safe in pre-clinical models, including in severely immunocompromised mice, and to be genetically stable after serial passages in vitro and in vivo for at least 12 months. It protects mice against *B. pertussis* challenge after a single nasal administration, both via protective CD4+ T cells and antibodies, and protection was shown to be long lived after a single nasal vaccination. It also has recently been shown to reduce nasopharyngeal infection by *B. pertussis* in baboons by 99.992% compared to non-vaccinated baboons. BPZE1 has now successfully completed a first-in-man phase I clinical trial and was found to be safe in human adults, able to transiently colonize the human nasopharynx and to induce immune responses to all tested antigens in all colonized individuals.

*B. pertussis* produces two serologically distinct fimbriae, composed of either Fim2 or Fim3 as the major fimbrial subunit. These fimbriae are involved in the attachment of the bacteria to respiratory epithelial cells. While BPZE1 produces only Fim2, it also produces hundreds of other antigens (e.g., pertussis toxin, FHA, and pertactin). It thus has been shown to induce significant protection against a wide array of *B. pertussis* clinical isolates, including those, which only produce Fim3.

SUMMARY

Described herein is the development of BPZE1f3, deposited with the Collection Nationale de Cultures de Microorganismes (CNCM, Institut Pasteur, 25 rue du Docteur Roux, F-75724 Paris Cedex 15, FRANCE) on Oct. 11, 2017 under registration number CNCM I-5247, a *B. pertussis* strain derived from BPZE1 that produces both serotype 2 fimbriae (Fim2) and serotype 3 fimbriae (Fim3). Given that BPZE1 produces several hundred different non-fimbriae antigens that could be targeted by immune responses, adding a single new antigen was not expected to have much effect on the protective effect of the bacteria. It was thus surprisingly discovered that vaccination with BPZE1f3 significantly improved the protective effect against certain clinical isolates which produce Fim3 and not Fim2.

In the study described in the Examples section below, an intranasal mouse challenge model was used to examine the protective potential of Fim2-producing BPZE1 and Fim2-, 3-producing BPZE1f3 to protect against clinical isolates of different serotypes. Both vaccine strains appeared to induce significant protection against all examined clinical isolates. However, BPZE1f3 provided significantly better protection than BPZE1 against a clinical isolate that only produced Fim3, confirming sero-specific protection to a certain degree.

A number of Fim2 and Fim3 subtypes have been identified. These include two Fim2 subtypes, Fim2-1, Fim2-2, which vary from each other by a single amino acid difference. Fim2-1 carries an arginine at position 174, whereas this is changed to a lysine in Fim2-2. The Fim3 subtypes are encoded by 6 different alleles. Fim3-2 differs from Fim3-1 by a single amino acid substitution at position 87: Alanine and Glutamate for Fim3-1 and Fim3-2, respectively. Fim3-3 carries, in addition to the Glutamate substitution at position 87, a change from Threonine in Fim3-1 to Alanine in Fim3-3. The fim3-4 allele differs from fim3-1 only by a single silent nucleotide polymorphism, whereas the other five alleles vary by three codons, each leading to one amino acid change in the major fimbrial subunit. Given the minor sequence differences between the various subtypes, it is likely that BPZE1f3 is protective against all of them.

To induce immune responses to fimbrial antigens, production of these antigens must be sufficiently stable in live *B. pertussis* vaccine strains. The stability of the Fim2 and Fim3 production deserves particular attention, since phase variation from one serotype to another has been described, especially during infection, and can be driven by vaccine pressure. This phase transition from high to low fimbrial production depends on the number of cytosines present in a C-string within the fim promoter region. The number of cytosines within this C-string may affect the distance between the −10 box of the fim promoters and the binding site of BvgA, the transcriptional activator required for the expression of fim and other *B. pertussis* virulence genes. It has long been known that DNA regions with repeated base pairs sequences, predominantly in C-strings, are particularly prone to additions or deletions of a single base. Since BPZE1f3 was constructed by the addition of a single C:G base pair in a stretch of 13 C in the promoter region to allow for fim3 expression, it was thought that the fim3 expression would be unstable. Unexpectedly, however, after several passages of BPZE1f3 through mice, 100% of the bacteria recovered after the first passage remained Fim3+, as well as Fim2+. During subsequent passages (up to 3), close to 90% of the bacteria still expressed both fim3 and fim2, indicating that fim expression was sufficiently stable to induce serotype-specific immunity, as confirmed by the protective effect of BPZE1f3 against Fim3-only producing clinical isolates.

Accordingly, described herein is a live attenuated *Bordetella* strain engineered to stably produce Fim3, wherein the live attenuated *Bordetella* strain retains the ability to colonize a mammalian subject's lungs and induce a protective immune response against *Bordetella* infection (e.g., the *Bordetella* strain designated BPZE1f3). The live attenuated *Bordetella* strain can be one that also stably produces Fim2. The live attenuated *Bordetella* strains described herein can also be rendered deficient in at least one (1, 2, or 3) of the following virulence factors: a functional pertussis toxin (PTX), a functional dermonecrotic toxin (DNT), and a functional tracheal cytotoxin (TCT).

Also described herein are vaccines that include a live attenuated *Bordetella* strain engineered to stably produce Fim3 mentioned herein and a pharmaceutically acceptable carrier. The vaccine can be provided in a single dosage form which includes at least $1 \times 10^6$ (e.g., at least $1 \times 10^6$, $5 \times 10^6$, or $1 \times 10^7$) colony forming units (CFU) of the strain.

Further described herein are methods of protecting a mammalian subject (e.g., a human being) from developing pertussis, which include the step of administering to the mammalian subject a vaccine including a pharmaceutically acceptable carrier and a live attenuated *Bordetella* strain engineered to stably produce Fim3, wherein the live attenuated *Bordetella* strain retains the ability to colonize a mammalian subject's lungs and induce a protective immune response against *Bordetella* infection.

As used herein, a bacterial strain that "stably produces" an antigen is one that can be passaged at least once (e.g., 1, 2, 3, 4, 5 or more times) through a host animal without losing more than 50% (or more than 60, 70, 80, 90, 95, 97, 98, or 99%) of the expression of that antigen. For example, an isolated *Bordetella* bacterial strain engineered to stably produce Fim3 is one that has been genetically modified to express Fim3, and retain at least 50% (e.g., 50, 60, 70, 80, 90, 95, 97, 98, or 99%) of the expression of Fim-3 after being passaged through a mouse, e.g., by the methods described in the Examples section below.

Reference to a "functional" virulence factor means that a bacterial strain possesses at least 50% of the enzymatic activity of that virulence factor compared to a the wild-type version of that virulence factor. A bacterial strain that "has been rendered deficient in at least one virulence factor" is a strain engineered to express less than 70, 80, 90, 95, 96, 97, 98, or 99% of the enzymatic or functional activity of that virulence factor as compared to the parent strain from which is was derived.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1A:
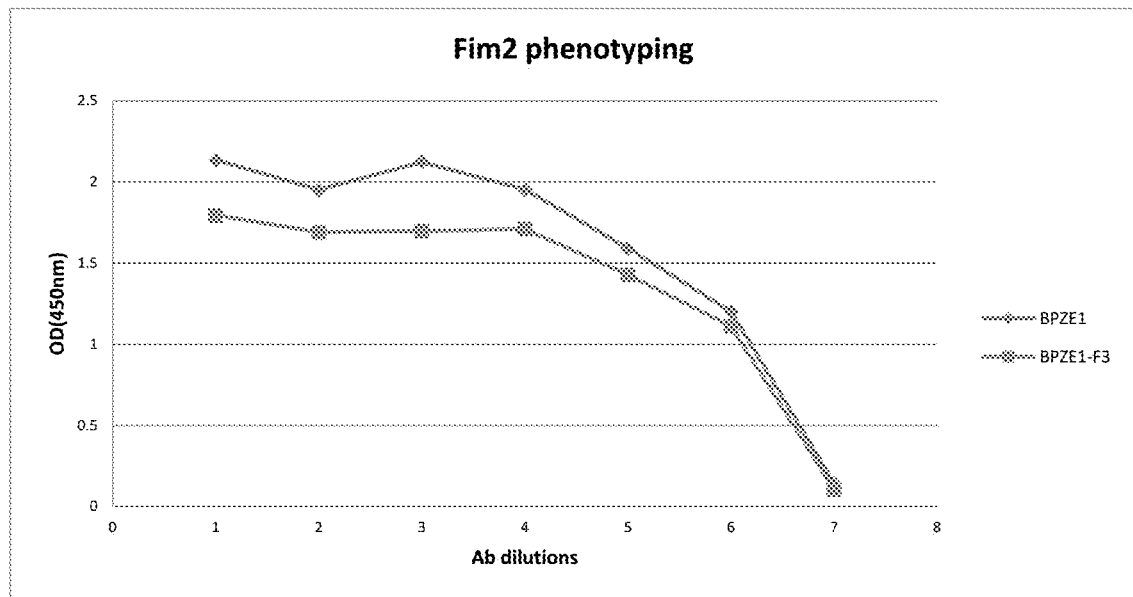
FIG. 1A is a graph showing the production of Fim2 by BPZE1 (in diamonds) and BPZE1f3 (in squares).

Described herein is a Fim3-producing BPZE1 derivative with sufficiently stable fim3 expression to provide improved protection in mice against Fim3-only producing clinical *B. pertussis* isolates. The fim3 expression in BPZE1f3 did not alter the protective efficacy against Fim2+ strains, nor against strains that produce neither Fim2 nor Fim3. The below described embodiments illustrate representative examples of these methods. Nonetheless, from the description of these embodiments, other aspects of the invention can be made and/or practiced based on the description provided below.

General Methodology

Methods involving conventional microbiological, immunological, molecular biological, and medical techniques are described herein. Microbiological methods are described in Methods for General and Molecular Microbiology (3d Ed), Reddy et al., ed., ASM Press. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008.

Fim3-producing *Bordetella* Strains

*Bordetella* species (e.g., *Bordetella pertussis, Bordetella parapertussis*, and *Bordetella bronchiseptica*) that lack Fim3 expression can be engineered to produce Fim3 (e.g., Fim3-1, Fim3-2, Fim3-3, or Fim3-4), and otherwise attenuated as described below. These Fim3-producing bacteria might be used to treat and/or prevent symptomatic or asymptomatic respiratory tract infections caused by *Bordetella* species as well as other conditions where BPZE1 was shown to be effective (e.g., allergy and asthma). *Bordetella* strains engineered to produce Fim3 might also be used to prevent transmission of *Bordetella* infections. Attenuated, Fim2-/Fim3-producing *Bordetella pertussis* is preferred for use in human subjects. *Bordetella* strains for use in making Fim3-producing bacteria can be isolated from natural sources (e.g., colonized subjects) or obtained from various culture collections. *Bordetella* strains that have been engineered to produce Fim3 can be made by the methods described below.

Because insufficient attenuation of a pathogenic strain of *Bordetella* might cause a pathological infection in a subject, it is preferred that the *Bordetella* strain engineered to produce Fim3 have lower levels of other virulence factors. On the other hand, to ensure that the Fim3-producing *Bordetella* strains are able to colonize a subject and exert a protective effect on respiratory tract inflammation, it must not be overly attenuated. Attenuation might be achieved by mutating the strain to reduce its production of one or more (e.g., 1, 2, 3, 4, 5 or more) of the following: pertussis toxin (PTX), dermonecrotic toxin (DNT), tracheal cytotoxin (TCT), adenylate cyclase (AC), lipopolysaccharide (LPS), filamentous hemagglutinin (FHA), pertactin, or any of the bvg-regulated components. Methods for making such mutants are described herein and in U.S. Pat. No. 9,119,804 and U.S. patent application Ser. No. 15/472,436. In the experiments presented below, a *Bordetella* strain was engineered to produce Fim3 that was deficient in DNT and TCT and produced genetically inactive PTX. It was able to colonize the respiratory tract of and induce a protective immune response in, subjects.

Formulations/Dosage/Administration

The *Bordetella* strains engineered to produce Fim3 can be formulated as a vaccine for administration to a subject. A suitable number of live bacteria are mixed with a pharmaceutically suitable excipient or carrier such as phosphate buffered saline solutions, distilled water, emulsions such as an oil/water emulsions, various types of wetting agents sterile solutions and the like. In some cases the vaccine can be lyophilized and then reconstituted prior to administration. The use of pharmaceutically suitable excipients or carriers which are compatible with mucosal (particularly nasal, bronchial, or lung) administration are preferred for the purpose of colonizing the respiratory tract. See Remington's Pharmaceutical Sciences, a standard text in this field, and in USP/NF.

When formulated for mucosal administration, each dose of the vaccine can include a sufficient number of live *Bordetella* bacteria to result in colonization of the respiratory tract, e.g., approximately (i.e., +/− 50%) $5\times10^{3}$ to $5\times10^{9}$ bacteria, depending on the weight and age of the mammal receiving it. For administration to human subjects, the dose can include approximately $1\times10^{6}$, $5\times10^{6}$, $1\times10^{7}$, $5\times10^{7}$, $1\times10^{8}$, $5\times10^{8}$, $1\times10^{9}$, $5\times10^{9}$, or $1\times10^{1}$ live Fim3-producing *Bordetella* bacteria. The dose may be given once or on multiple (2, 3, 4, 5, 6, 7, 8 or more) occasions at intervals of 1, 2, 3, 4, 5, or 6 days or 1, 2, 3, 4, 5, or 6 weeks, or 1, 2, 3, 4, 5, 6, or 12 months. Generally, sufficient amounts of the vaccine are administered to result in colonization and the protective response. Additional amounts are administered after the induced protective response wanes.

Methods of Eliciting Immune Responses to Protect Against Pertussis

The vaccines described herein can be administered to a mammalian subject (e.g., a human being, a human child or neonate, a human adult, a human being at high risk from developing complications from pertussis, a human being with lung disease, and a human being that is or will become immunosuppressed) by any suitable method that deposits the bacteria within the vaccine in the respiratory tract. For example, the vaccines may be administered by inhalation or intranasal introduction, e.g., using an inhaler, a syringe, an insufflator, a spraying device, etc. While administration of a single dose of between 1×10$^4$ to 1×10$^7$ (e.g., 1×10$^4$, 5×10$^4$, 1×10$^5$, 5×10$^5$, 1×10$^6$, 5×10$^6$, or 1×10$^7$+/− 10, 20, 30, 40, 50, 60, 70, 80, or 90%) live bacteria is typically sufficient to induce protective immunity against developing a *Bordetella* infection such as pertussis, one or more (1, 2, 3, 4, or more) additional doses might be administered in intervals of 4 or more days (e.g., 4, 5, 6, or 7 days; or 1, 2 3, 4, 5, 6, 7, or 8 weeks) until a sufficiently protective immune response has developed. The development of a protective immune response can be evaluated by methods known in the art such as quantifying *Bordetella*-specific antibody titers and measuring of *Bordetella* antigen-specific T cells responses (e.g., using an ELISPOT assay). In cases were a vaccine-induced protective immune response has waned (e.g., after 1, 2, 3, 4, 5, 10 or more years from the last vaccination) a subject may again be administered the vaccine in order to boost the anti-*Bordetella* immune response.

EXAMPLES

Materials and Methods

Culture Conditions

All *B. pertussis* strains were grown on Bordet Gengou (BG) agar with 10% (v/v) sheep blood, in modified Stainer Scholte (SS) medium under agitation as described (Imaizumi et al., Infect Immun 1983; 41:1138-43) or in fully synthetic Thijs medium (Thalen et al., J Biotechnol 1999; 75:147-59). The media were supplemented with the appropriate antibiotics (100 ug/ml of streptomycin or 10 ug/ml of gentamycin for the strains carrying pFUS2 BctA1).

Bacterial Strains

*B. pertussis* BPSM and BPZE1, as well as *Bordetella parapertussis* used in this study have been described previously (Mielcarek et al., PLoS Pathog 2006; 2:e65; Menozzi et al., Infect Immun 1994; 62:769-78). *B. pertussis* strains B0403, B1412, B1617 and B0005 (strain 134 Pillmer) came from the RIVM collection (Bilthoven, The Netherlands). For counter-selection purposes some of the clinical isolates strains were electroporated with the pFUS2 BctA1 suicide plasmid to acquire the gentamycin resistance as described in Antoine et al. (J Mol Biol 2005; 351:799-809). Gentamycin-resistant derivatives after electroporation were checked by PCR to verify the site of insertion of the pFUS2 BctA1 vector into the chromosomal DNA and by ELISA to check the level of surface exposed Fim2 and/or Fim3, as described below. Strain P134S was obtained by selecting a streptomycin derivative of *B. pertussis* B0005. Strain P134S carries, in addition to streptomycin resistance mediated by a mutation in the rpsl gene, a mutation in the fimC gene leading to the loss of the fimbriae production. *Escherichia coli* SM10 (Simon et al., Bio/Technology 1983; 1:784-91) was used for conjugation of the various plasmid constructs into *B. pertussis*.

Construction of the Fim3-Positive BPZE1-Derivative BPZE1f3

To construct BPZE1f3, the 13 C stretch located in the promoter region of the fim3 gene of BPZE1, 75 bp upstream of the fim3 ATG codon, was replaced by a 14 C stretch in order to trigger the transcription of fim3. The whole fim3 locus, containing the promoter region, was first deleted in the parental strain and then replaced by a fim3 locus with a 14 C stretch. A 2265-bp PCR fragment encompassing the locus was amplified by using the following oligonucleotides (SPfim3UP2: GAGCTCTTTACCGCGGCCGCCAGTTGTTCATCAATG (SEQ ID NO: 1) and ASPfim3LO2: GGATCCATCATCGAGACCGACTGG (SEQ ID NO: 2)) and cloned into the SacI and BamHI restriction sites of a pBluescript II SK+ plasmid (Addgene). From resulting plasmid, a 904-bp fragment containing the whole locus was removed by SphI restriction to obtain pSKfim3UPLO. The 1351-bp SacI-BamHI fragment of pSKfim3UPLO was inserted into the SacI and BamHI sites of pJQ200mp18rpsL (Antoine, J. Mol. Biol. (2005) 351,799-809). The recombinant plasmid was then used for double homologous recombination in BPZE1 using conjugation as described previously (Mielcarek et al., PLoS Pathog 2006; 2:e65). The transconjugants were checked for deletion of the whole fim3 locus by PCR using oligonucleotides SPfim3UP2 and ASPfim3LO2. Reintroducing the whole fim3 locus with the 14 C stretch in the promoter was done as follows. A 911-bp synthetic gene encompassing the whole locus with the 14 C stretch was synthesized by GeneArt® Gene Synthesis (ThermoFisher SCIENTIFIC). SphI sites at the extremities of the synthetic fragment were used to insert it into the SphI site of pSKfim3UPLO giving rise to pSKfim3+. The correct orientation of the insert was checked by restrictions. The 2256-bp SacI-BamHI fragment of this plasmid was transferred into the same restriction sites of pJQ200mp18rpsL leading to pJQfim3+. This plasmid was used to do the double homologous recombination to obtain BPZE1f3. The recombinant strain was verified by PCR using oligonucleotides SPfim3UP2 and ASPfim3LO2.

Analysis of Fim2 and Fim3 Production

The *B. pertussis* strains were first inactivated by heating at 56° C. for 30 minutes. The heat-inactivated strains were then coated at an optical density (OD) 600 nm of 0.075 in 96-well plates (Nunc Maxi Sorp,) and incubated overnight at 37° C. until the wells were dry. The wells were then blocked with 100 µl of PBS Tween 0.1% (PBST), containing 1% of Bovine Serum Albumin (BSA). Fim2 and Fim3 monoclonal antibodies (NIBSC, 04/154 and 04/156, respectively) were added in serial dilutions from 1/50 to 1/36450 in PB ST (v/v). After three washes, the plates were incubated with 100 µl of horseradish-peroxidase-labeled goat anti-mouse IgG (Southern Biotech) in PBST. Following five washes, the plates were incubated with 100 µl of HRP Substrate TMB solution (Interchim) for 30 min at room temperature. The reaction was stopped by the addition of 50 µl of 1 M $H_3PO_4$. The OD was measured with a Biokinetic reader EL/340 microplate at 450 nm.

DNA Sequencing

PCR amplification of chromosomal DNA was performed using Phusion High-Fidelity DNA Polymerase (Thermofisher) or KAPA HiFi DNA Polymerase (Kapa Biosystems) according to the manufacturer's instructions. The PCR fragments were purified with a QiaQuick PCR purification kit (Qiagen) and sequenced with the primers used for amplification. Primers ptxP Up and ptxP Low used for PCR amplification of ptxP have been described previously (Mooi et al., Emerg Infect Dis 2009; 15:1206-13). Primers prn AF and prn AR used for partial PCR amplification of prn has been described previously (Mooi et al., Infect Immun 1998; 66:670-5). Primers fim2 Up 5'-AGCTAGGGGTAGAC-CACGGA-3' (SEQ ID NO: 3) and fim2 Low 5'-ATAACTCTTCTGGCGCCAAG-3' (SEQ ID NO: 4) were used for amplification and sequencing of fim2. Primers fim3 Up 5'-CATGACGGCACCCCTCAGTA-3' (SEQ ID NO: 5) and fim3 Low 5'-TTCACGTACGAGGCGAGATA-3' (SEQ ID NO: 6) were used for amplification and sequencing of fim3.

Mouse Infection Experiments

BALB/c mice were obtained from Charles River (l'Abresle, France) and maintained under specific pathogen-free conditions in the animal facilities of the Institut Pasteur de Lille. Six week-old BALB/c mice were lightly sedated by intraperitoneal injection with an anesthetic cocktail (ketamine+atropine+valium) before intranasal (i.n.) administration with 20 μl PBS containing $10^6$ colony-forming units (CFU) of B. pertussis BPZE1 or BPZE1f3, as previously described (Mielcarek et al., PLoS Pathog 2006; 2:e65). Three mice per group were sacrificed at selected time points after i.n. administration, and their lungs were harvested, homogenized in PBS and plated in serial dilutions onto BG-blood agar to count CFUs after incubation at 37° C. for three to four days.

Mouse Protection Experiments

Six week-old BALB/c mice were i.n. vaccinated with $10^5$ CFU of B. pertussis BPZE1 or BPZE1f3, as described above. Four weeks later, naïve and vaccinated mice were challenged with $10^6$ CFU of B. pertussis BPSM, the indicated clinical B. pertussis isolates or B. parapertussis in 20 μl of PBS. Lung colonization was determined 3 h and 7 days later with 3 and 5 mice per group, respectively.

Stability of Fim3 and Fim2 Production $10^6$ CFUs of BPZE1f3 were administered to a sedated mouse in 20 μl of PBS. 14 days later, the lung was harvested, homogenized and plated onto BG agar. 3-4 days later, 94 individual colonies were inoculated into a 96-well plate containing 100 μl of PBS/well. Control wells contained BPZE1, as a negative control, and BPZE1f3 as a positive control. The amount of bacteria present in each well was determined by OD measurement at 630 nm. After drying, the presence of Fim3 and of Fim2 was evaluated by whole-cell ELISA as described above. After a blocking step with 100 μl PBST containing 1% BSA, bacteria were incubated during one hour with the anti-Fim3 monoclonal antibody 04/156 or anti-Fim2 monoclonal antibody 04/154 at a 1/1350 dilution in 100 μl PBST. After washes and incubation with 100 μl of horseradish-peroxidase-labeled goat anti-mouse IgG (Southern Biotech) in PBST, the presence of Fim3 or Fim2 was evaluated with 100 μl of HRP Substrate TMB solution (Interchim) revelation. The reaction was stopped by the addition of 50 μl of 1 M $H_3PO_4$. The OD was measured with a Biokinetic reader EL/340 microplate at 450 nm.

Results

Construction of BPZE1f3

In order to construct a BPZE1 derivative that produces Fim3, the fim3 gene was first deleted from BPZE1. The upstream and downstream flanking regions of fim3 were amplified by PCR using the BPZE1 chromosomal DNA as template and were spliced together in the non-replicative vector pJQ200mp 18rpsL (Antoine, J. Mol. Biol. (2005) 351, 799-809). The fim3 gene of BPZE1 was then deleted by allelic exchange after conjugation with E. coli SM10 containing the recombinant plasmid. The resulting strain BPZE1Δfim3 was used to re-integrate the fim3 gene together with a functional promoter into the original fim3 locus. The 13-C stretch of the original promoter was replaced by a 14-C stretch, allowing for fim3 expression and inserted into pSKfim3UPLO together with the fim3 open reading frame. The resulting plasmid pJQFim3+ was conjugated into BPZE1Δfim3 via conjugation with E. coli SM10: pJQFim3+. This resulted in BPZE1f3.

Figure 1B:
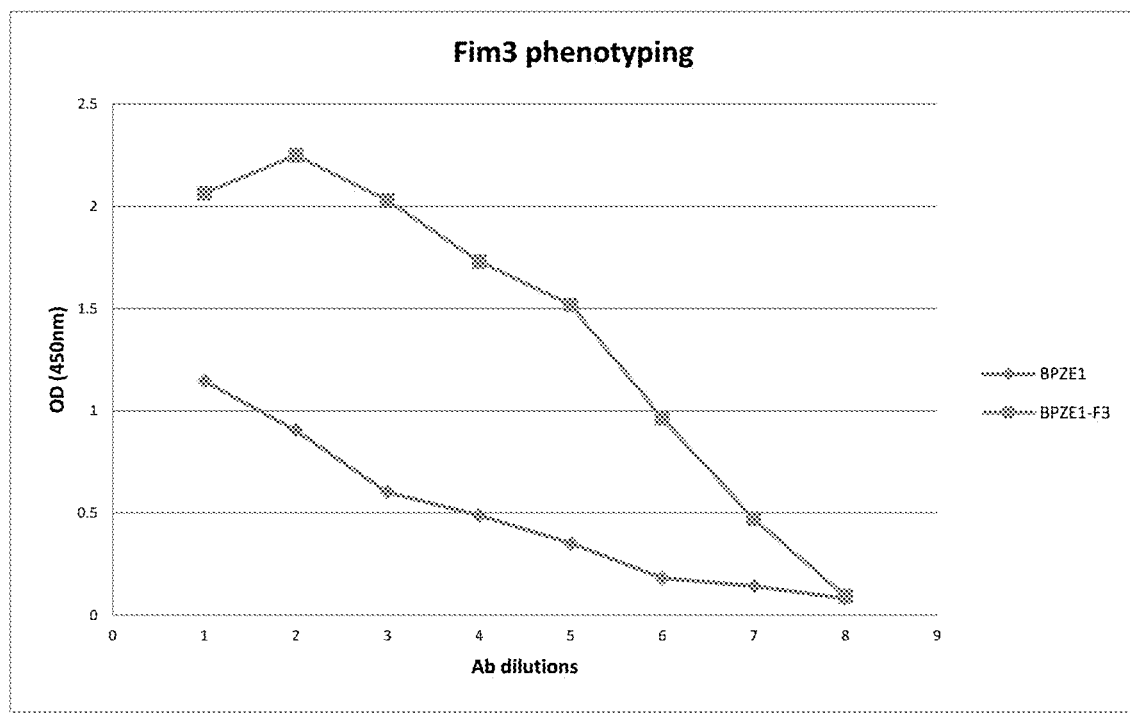
FIG. 1B is a graph showing the production of Fim3 by BPZE1 (in diamonds) and BPZE1f3 (in squares).
Figure 2A:
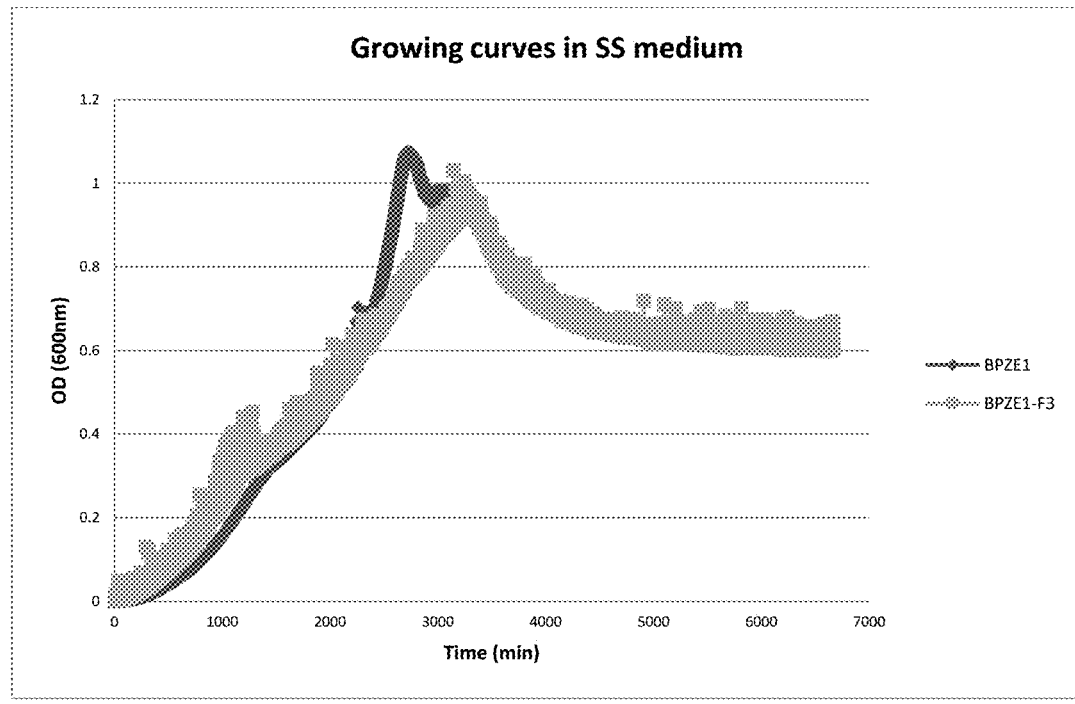
FIG. 2A is a graph showing the in vitro growth of BPZE1 (in diamonds) and BPZE1f3 (in squares) in modified Stainer-Scholte medium.
Figure 2B:
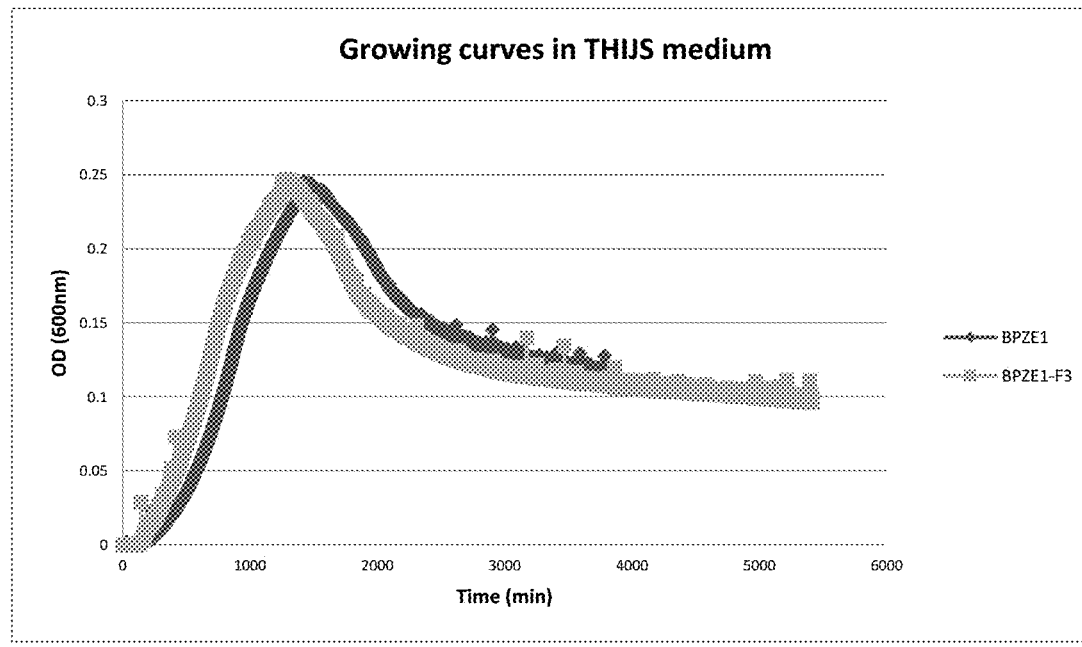
FIG. 2B is a graph showing the in vitro growth of BPZE1 (in diamonds) and BPZE1f3 (in squares) in fully synthetic Thijs medium.

The production of Fim2 and Fim3 in BPZE1f3 was analyzed by whole-cell ELISA using Fim2-specific and Fim3-specific monoclonal antibodies, respectively. As shown in FIG. 1A, both BPZE1 and BPZE1f3 produced equivalent amounts of Fim2. In contrast, Fim3 was only produced by BPZE1f3, and only background absorbency was detected with the Fim3-specific antibody on whole BPZE1 extracts (FIG. 1B). Both strains grew equally well in Stainer Scholte medium and in the completely synthetic Thijs medium (FIG. 2), indicating that the production of Fim3 did not affect the growth characteristics of BPZE1f3.

Mouse Colonization by BPZE1f3.

Figure 3:
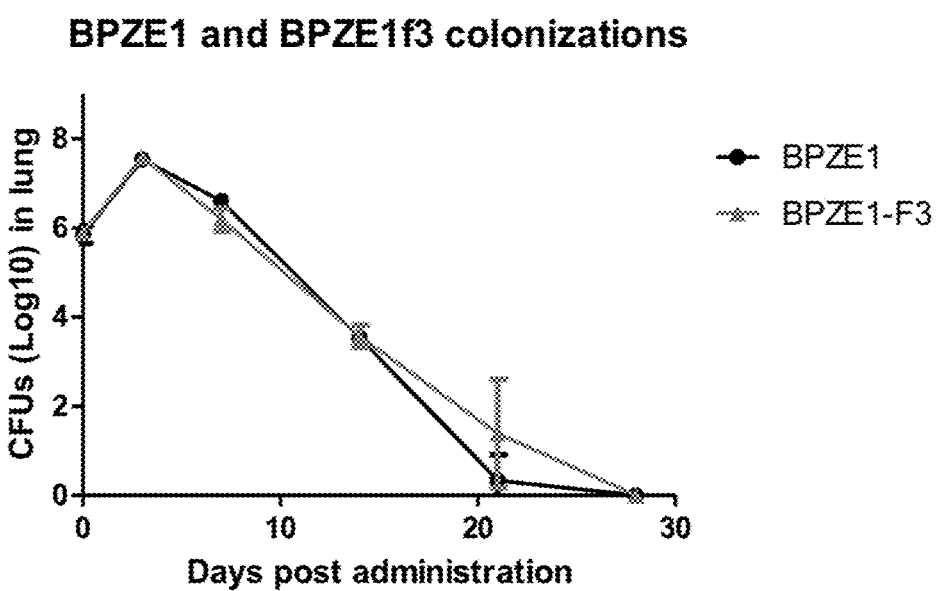
FIG. 3 is a graph showing lung colonization of mice nasally inoculated with $10^6$ CFU of BPZE1 (in black) or BPZE1f3 (in grey), where the bacterial loads in the lungs were measured at the indicated time points.
Figure 4A:
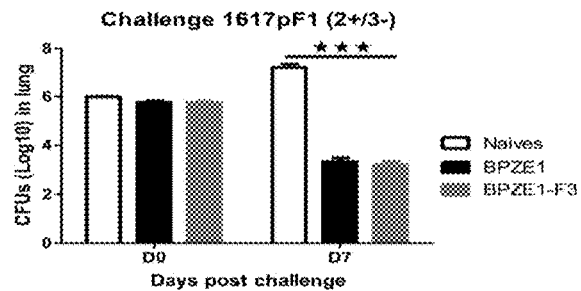
FIGS. 4A-4E represent a series of graphs showing BPZE1- and BPZE1f3-induced protection against clinical *B. pertussis* isolates where mice received nasally either $10^5$ CFU of BPZE1 (black bars) or BPZE1f3 (grey bars), or were left untreated (white bars). Four weeks after vaccination the mice were challenged with $10^6$ CFU of 1617pF1 (A), 403pF1 (B), P134 (C), 1412pF1 (D) or 403pF3 (E). Three h (left part of the panels, D0) or 7 days (right part of the panels, D7) after challenge, the bacterial loads in the lungs were measured and are presented as means and standard deviations of CFU. Three (for D0) or five (for D7) mice per group were used. ***, $p<0.001$.
Figure 4B:
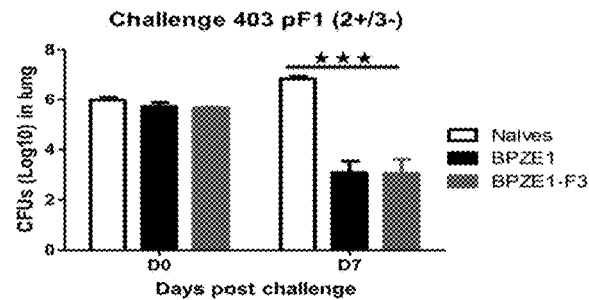
Figure 4C:
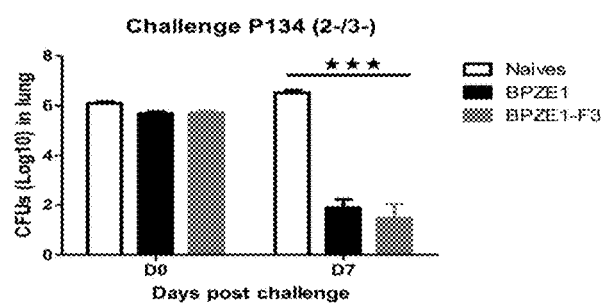
Figure 4D:
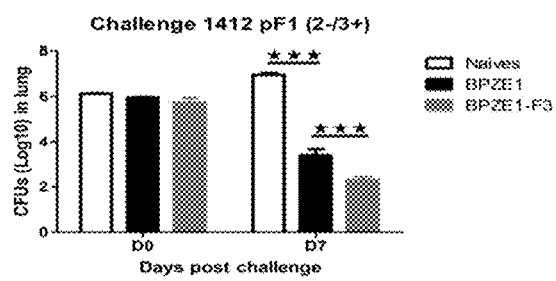
Figure 4E:
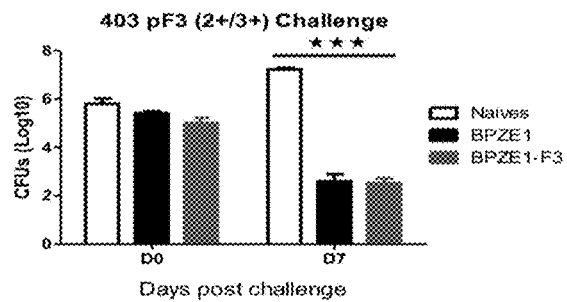

To assess the potential role of Fim3 production by BPZE1f3 in the colonization of the mouse respiratory tract, adult mice were infected with $10^6$ CFU of either BPZE1 or BPZE1f3, and 3 mice per group were sacrificed at days 3, 7, 14, 21 and 28 post-infection to quantify the bacterial loads in their lungs. As shown in FIG. 3, the capacity to colonize the mouse lungs was identical between the two strains at all time points analyzed, indicating that the production of Fim3 did not enhance, nor hamper the ability of BPZE1 to colonize the murine respiratory tract.

BPZE1- and BPZE1f3-Mediated Protection Against Clinical B. Pertussis Isolates

To examine the relative protective effects of BPZE1 and BPZE1f3 against clinical isolates that differ with respect to their production of Fim2 and Fim3, we used a sub-optimal immunization protocol, in which mice were intranasally immunized with $10^5$ CFU of the vaccine strains and infected one month later with $10^6$ CFU of the challenge strains. This protocol was used because it is best suited to detect potential differences between vaccine lots, as the standard vaccination protocol using $10^6$ CFU of the vaccine strain followed two months later by infection with $10^6$ CFU of the challenge strain usually results in total clearance 7 days after challenge.

The potency of the two vaccine strains was tested against four different clinical isolates from the B. pertussis culture collection of the RIVM (Bilthoven, The Netherlands). The five strains had the following characteristics with respect to Fim2 and Fim3 production: 1617F1 (Fim2+Fim3−), 403pF1 (Fim2+Fim3−), P134 (Fim2−Fim3−), 1412pF1 (Fim2−Fim3+) and 403pF3 (Fim2+Fim3+). The genomic key features of these strains are presented in table I below. After vaccination and challenge infection the bacterial load of the challenge strain was measured in the lungs 3 h and 7 days after infection.

TABLE I

Key genomic features of the B. pertussis strains.

| | Pptx[1] | fim2 | fim3 | serotype | Prn[3] | ptx-s1[4] |
|---|---|---|---|---|---|---|
| BPSM | P1 | fim2-1[2] | fim3-1[2] | 2+/3− | prn-1 | ptxA2 |
| BPZE1 | P1 | fim2-1 | fim3-1 | 2+/3− | prn-1 | ptxA2 (R9K, E129G) |
| BPZE1f3 | P1 | fim2-1 | fim3-1 | 2+/3+ | prn-1 | ptxA2 (R9K, E129G) |
| B1412 pF1 | P1 | fim2-1 | fim3-1 | 2−/3+ | prn-1 | ptxA1 |
| B1617 pF1 | P1 | fim2-1 | fim3-1 | 2+/3− | prn-1 | ptxA1 |
| B0403 pF1 | P1 | fim2-1 | fim3-1 | 2+/3− | prn-1 | ptxA2 |
| B0403 pF3 | P1 | fim2-1 | fim3-1 | 2+/3+ | prn-1 | ptxA2 |
| P134S | P1 | fim2-1 | fim3-1 | 2−/3− | prn-1 | ptxA2 |

[1]Promoter type of the pertussis toxin gene.
[2]Fimbrial gene genotype
[3]Pertactin gene allele
[4]Pertussis toxin subunit S1 allele BPZE1 and BPZE1f3 protected equally well against 1617pF1, 403pF1, P134 and 403pF3, diminishing the bacterial loads in each case by 4 to 5 logs at 7 days post-infection, compared to the bacterial loads in non-vaccinated mice (FIG. 4). There was no statistically significant difference between BPZE1-vaccinated and BPZE1f3-vaccinated mice. However, when the mice were challenged with 1412pF1, the strain that only produces Fim3 and not Fim2, BPZE1f3 appeared to protect significantly better than BPZE1 (FIG. 4D). Whereas BPZE1 vaccination resulted in a 4 log difference in bacterial load compared to non-vaccinated mice, BPZE1f3 increased this protection to a 5 log difference. No statistically significant decrease in bacterial loads between vaccinated and non-vaccinated mice was observed when the CFU were measured 3 h after challenge infection, indicating that, as expected, all the mice had received the same challenge dose. These results indicate improved potency of BPZE1f3 over BPZE1 against strains that only produce Fim3, whereas there is no improvement in protection against strains that produce Fim2 with or without Fim3, or against strains that do not produce fimbriae.

BPZE1- and BPZE1f3-Mediated Protection Against *Bordetella parapertussis*

Figure 5:
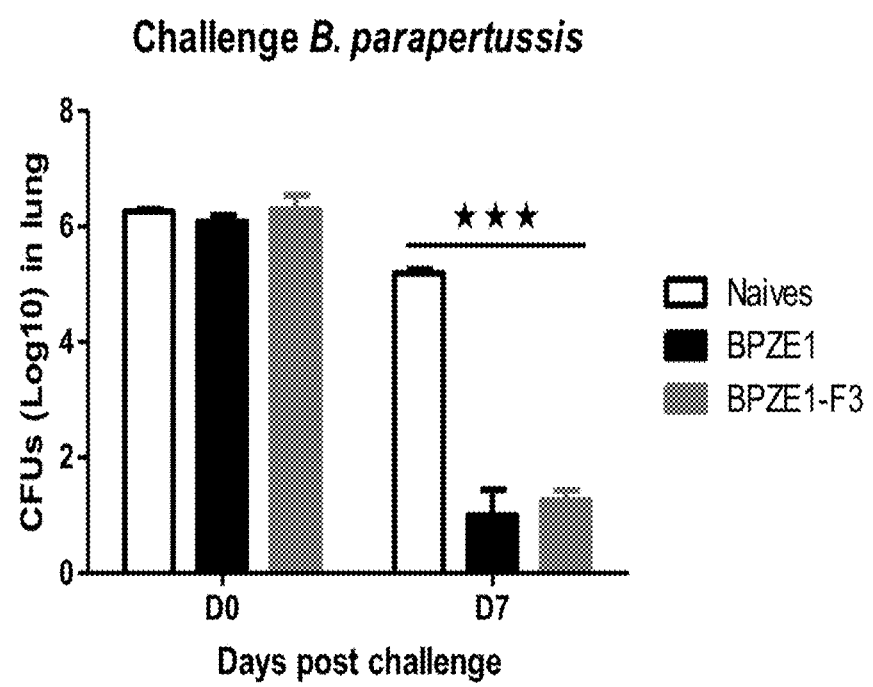
FIG. 5 is a graph comparing BPZE1- and BPZE1f3-induced protection against *B. parapertussis* where mice received nasally either $10^6$ CFU of BPZE1 (black bars) or BPZE1f3 (grey bars), or were left untreated (white bars). Two months after vaccination the mice were challenged with $10^6$ CFU of *B. parapertussis*. Three h (left part of the panel, D0) or 7 days (right part of the panel, D7) after challenge, the bacterial loads in the lungs were measured and are presented as means and standard deviations of CFU. Three (for D0) or five (for D7) mice per group were used. ***, p<0.001.

The potency of BPZE1f3 against *B. parapertussis* was also tested. In this case, $10^6$ CFU of the vaccine strain was used, followed by challenge with $10^6$ CFU of *B. parapertussis* two months after vaccination. It was previously shown that this protocol leads to strong protection, although not to total clearance 7 days after challenge infection (Mielcarek et al., PLoS Pathog 2006; 2:e65). Seven days after *B. parapertussis* infection, both BPZE1- and BPZE1f3-vaccinated mice showed a strong reduction in bacterial load in the lungs (between 4 and 5 logs.) compared to non-vaccinated mice (FIG. 5). No statistical difference was seen between BPZE1- and BPZE1f3-vaccinated mice, indicating that the production of Fim3 does not offer an advantage, nor is it detrimental for protection against *B. parapertussis* infection.

Stability of Fim3 Production by BPZE1f3

Figure 6:
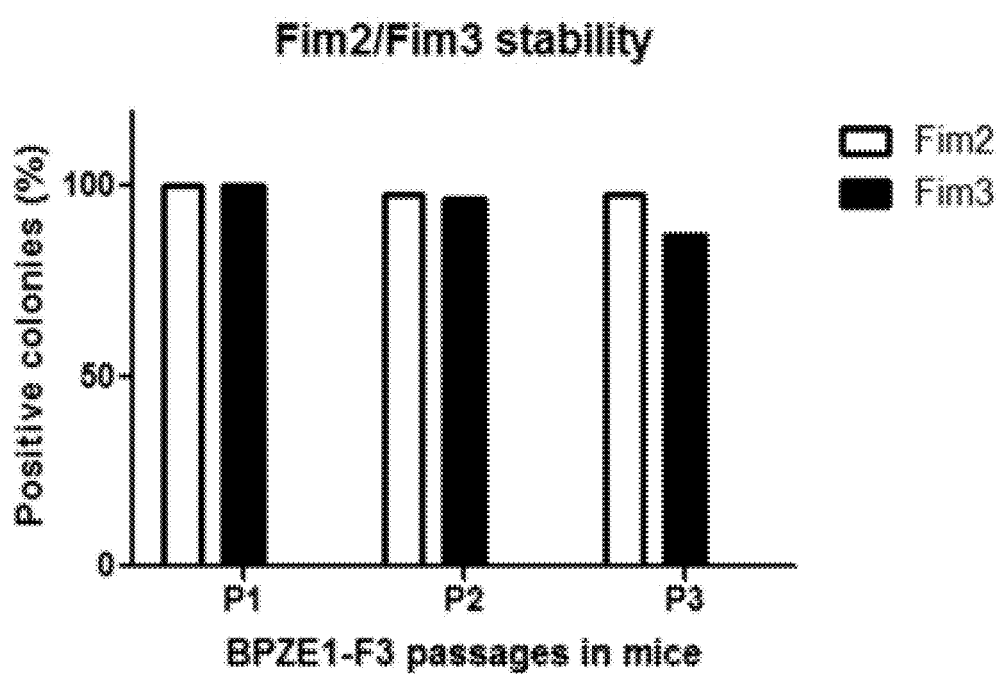
FIG. 6 is a graph showing the stability of Fim2 and Fim3 production by BPZE1f3, where BPZE1f3 was passaged three times in mice, and at each passage (P1 to P3), 94 colonies were analysed by whole-cell ELISA for the presence of Fim2 (white bars) and Fim3 (black bars) using anti-Fim2 and anti-Fim3 monoclonal antibodies.

Since the only genetic difference between BPZE1 and BPZE1f3 is the amount of C in the C-string of the fim3 promoter (13 C in BPZE1 and 14 C in BPZE1f3), and since C strings re prone to phase shift variation in *B. pertussis* (Willems et al., EMBO J 1990; 9:2803-9), the stability of both Fim3 and Fim2 production by BPZE1f3 was evaluated after in vivo passaging of the vaccine strain in mice. Mice were infected with $10^6$ CFU of BPZE1f3, and the bacteria present in the lungs 14 days after infection were harvested and plated onto BG agar. After growth, 94 individual colonies were inoculated into a 96-well plate. The remaining colonies were harvested and administered to mice for a second passage, followed 2 weeks later by a third passage. At each passage 94 individual colonies were inoculated into a 96-well plate containing 100 μl of PBS/well. Control wells contained BPZE1, as a negative control, and BPZE1f3 as a positive control. The amount of bacteria present in each well was determined by OD measurement at 630 nm. After drying, the presence of Fim3 and Fim2 was evaluated by whole-cell ELISA. 94 of the 94 clones were found to produce both Fim3 and Fim2 after the first passage. After the second passage 97.9% of the colonies produced Fim2 and 96.8% produced Fim3, and after the third passage the numbers were 87.23% and 97.9% for Fim3 and Fim2, respectively (FIG. 6), indicating a relatively stable fim3 expression, with only 12.77% loss after 3 in vivo passages.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A vaccine comprising a pharmaceutically acceptable carrier and a live attenuated *Bordetella pertussis* strain engineered to stably produce Fim3, wherein the live attenuated *Bordetella pertussis* strain retains the ability to colonize a mammalian subject's lungs and induce a protective immune response against *Bordetella* infection by *Bordetella pertussis* or *Bordetella parapertussis*, wherein the live attenuated *Bordetella* strain also stably produces Fim2.

2. The vaccine of claim 1, wherein the live attenuated *Bordetella pertussis* strain has been rendered deficient in at least one virulence factor selected from the group consisting of a functional pertussis toxin (PTX), a functional dermonecrotic toxin (DNT), and a functional tracheal cytotoxin (TCT).

3. The vaccine of claim 1, wherein the live attenuated *Bordetella pertussis* strain has been rendered deficient in at least two virulence factors selected from the group consisting of a functional PTX, a functional DNT, and a functional TCT.

4. The vaccine of claim 1, wherein the live attenuated *Bordetella pertussis* strain has been rendered deficient in a PTX, a functional DNT, and a functional TCT.

5. The vaccine of claim 1, wherein the vaccine is provided in a single dosage form which comprises at least $1 \times 10^6$ colony forming units (CFU) of the strain.

6. The *Bordetella* strain designated BPZE1f3 deposited with the Collection Nationale de Cultures de Microorganismes (CNCM) under Registration No. CNCM I-5247.

* * * * *